United States Patent [19]
Stavridi et al.

[11] Patent Number: 5,341,805
[45] Date of Patent: Aug. 30, 1994

[54] GLUCOSE FLUORESCENCE MONITOR AND METHOD

[75] Inventors: Marigo Stavridi; Warren S. Grundfest, both of Los Angeles, Calif.

[73] Assignee: Cedars-Sinai Medical Center, Los Angeles, Calif.

[21] Appl. No.: 43,580

[22] Filed: Apr. 6, 1993

[51] Int. Cl.$^5$ .............................................. A61B 5/00
[52] U.S. Cl. ................................... 128/633; 128/634; 356/39; 356/317; 356/320
[58] Field of Search ...................... 128/633.5, 664–667, 128/645–652, 745; 351/206–207, 221; 356/39–41, 317–320

[56] References Cited

U.S. PATENT DOCUMENTS

| | | | |
|---|---|---|---|
| 3,313,290 | 8/1963 | Chance et al. | |
| 3,706,612 | 10/1971 | Clemens | 356/178 |
| 3,830,222 | 8/1974 | Chance | |
| 3,975,098 | 8/1976 | West | 356/85 |
| 4,162,405 | 7/1979 | Chance et al. | 350/461 B |
| 4,170,987 | 10/1979 | Anselmo et al. | 128/665 |
| 4,178,917 | 12/1979 | Shapiro | 128/665 |
| 4,184,175 | 1/1980 | Mullane, Jr. | 358/93 |
| 4,236,526 | 12/1980 | Richard | 128/633 |
| 4,412,543 | 11/1983 | Vassiliadis et al. | 128/665 X |
| 4,449,535 | 5/1984 | Renault | 128/634 |
| 4,479,499 | 10/1984 | Alfano | 128/665 |
| 4,569,354 | 2/1986 | Shapiro et al. | 128/665 |
| 4,608,990 | 9/1986 | Elings | 128/633 |
| 4,629,693 | 12/1986 | Khanna | 435/7 |
| 4,631,413 | 12/1986 | Jensen et al. | 250/458.1 |
| 4,675,529 | 6/1987 | Kushida | 250/458.1 |
| 4,680,268 | 7/1987 | Clark, Jr. | 435/291 |
| 4,894,547 | 1/1990 | Leffell et al. | 250/461.2 |
| 4,928,694 | 5/1990 | Maxwell | 128/637 |
| 4,930,516 | 6/1990 | Alfano et al. | 128/665 |
| 4,951,669 | 8/1990 | Maxwell et al. | 128/637 |
| 4,957,114 | 9/1990 | Zeng et al. | 128/665 |
| 4,981,138 | 1/1991 | Deckelbaum et al. | 128/665 |
| 4,981,779 | 1/1991 | Wagner | 435/288 |
| 5,001,054 | 5/1991 | Wagner | 435/14 |
| 5,014,707 | 5/1991 | Schwartz | 128/633 |
| 5,034,189 | 7/1991 | Cox et al. | 422/52 |
| 5,037,738 | 8/1991 | Lamos et al. | 435/12 |

(List continued on next page.)

OTHER PUBLICATIONS

Pini et al., "Laser Dentistry: Root Canal Diagnostic Technique Based on Ultraviolet-Induced Fluorescence Spectroscopy", Lasers in Surgery and Medicine, vol. 9, pp. 358–361 (1989).

(List continued on next page.)

*Primary Examiner*—Angela D. Sykes
*Attorney, Agent, or Firm*—Pretty, Schroeder, Brueggemann & Clark

[57] ABSTRACT

A glucose monitor, and related method, determines the concentration of glucose in a sample by monitoring fluorescent light produced directly by any glucose present in the sample. The glucose monitor illuminates the sample with ultraviolet excitation light that induces any glucose present in the sample to fluoresce, with the fluorescent light being monitored and processed to determine the concentration of glucose in the sample. A sensor monitors the return light, which includes fluorescent light produced by any glucose in the sample, and generates first and second electrical signals indicative of the intensity of light in two wavelength bands. One wavelength band includes a characteristic spectral peak of glucose fluorescence, and the other wavelength band is a reference band having known spectral characteristics. A processor then processes the first and second electrical signals to determine the concentration of glucose in the sample. A fiber-optic waveguide is used to guide the excitation light from the laser light source to the sample and the return light from the sample to the sensor. The fiber-optic waveguide is housed in a catheter or probe that is adapted to monitor the concentration of glucose percutaneously in the oral cavity tissues of a person's mouth such as the gums.

19 Claims, 5 Drawing Sheets

U.S. PATENT DOCUMENTS

| | | | |
|---|---|---|---|
| 5,042,494 | 8/1991 | Alfano | 128/665 |
| 5,046,501 | 10/1991 | Crilly | 128/665 |
| 5,072,731 | 12/1991 | Taratula et al. | 128/665 X |
| 5,074,306 | 12/1991 | Green et al. | 128/664 |
| 5,093,266 | 3/1992 | Leader et al. | 436/68 |
| 5,101,814 | 4/1992 | Palti | 128/635 |
| 5,115,137 | 5/1992 | Andersson-Engles et al. | 128/634 X |
| 5,127,405 | 7/1992 | Alcala et al. | 128/633 |
| 5,172,693 | 12/1992 | Doody | 128/633 |
| 5,209,231 | 5/1993 | Cote et al. | 128/665 X |
| 5,217,456 | 8/1993 | Narcisco, Jr. | 606/15 |

OTHER PUBLICATIONS

Willenborg, "Dental Laser Applications: Emerging to Maturity", Lasers in Surgery and Medicine, vol. 9, pp. 309–313 (1989).

Bassnett et al., "Intracellular pH measurement using single excitation dual emission fluorescence ratios", Am. J. Physiol. 258, 1990, pp. C171–C178.

Ring et al., "In-Vitro Evaluation of New Fiber Optic pH, Carbon Dioxide, and Oxygen Sensor Systems", Date: unknown, 10 pgs.

Ring et al., "In-Vitro Evaluation of New Fiber Optic pH, Carbon Dioxide and Oxygen Sensor Systems", SPIE OE LASER '92, Conf. 1648, Jan. 1992, 11 pgs.

Green et al., "Burn Depth Estimation Using Indocyanine Green Fluorescence Arch Dermatol", vol. 128, Jan. 1992, pp. 43–49.

Moneta et al., "Infrared Fluorescence Videomicroscopy of Sking Capillaries With Indocynine Green", Int. J. Microcirc. Clin. Exp., pp. 25–34, (1987).

Gotti et al., "Evaluation of the Burn Wound with Perfusion Fluorometry", J. Trauma vol. 23, No. 3, Mar. 1983, pp. 202–206.

Afromowitz et al., "Multispectral Imaging of Burn Wounds", IEEE Trans. Biomed. Eng., vol. 35, No. 10, Oct. 1988, pp. 842–849.

Mendelson, et al., "Blood Glucose Measurement by Multiple Attenuated total Reflection and Infrared Absorption", IEEE Transactions on Biomedical Engineering, vol. 37, No. 5, May 1990, pp. 458–464.

Heiss, et al., "Multivariate Determination of Glucose in Whole Blood by Attentuated Total Reflection Infrared Spectroscopy", American Chemical Society, Analytical Chemistry, vol. 61, No. 18, Sep. 15, 1989, pp. 2009–2015.

Cooper, Gerald R., "Methods for Determining the Amount of Glucose in Blood", CRC Critical Review in Clinical Laboratory Services, Aug. 1973, pp. 101–145.

Tietz, Norbert W., "Determination of Glucose in Body Fluids", Fundamentals of Clinical Chemistry, 1987, pp. 426–430, 446–447.

Burrin, J. M. and Price, C. P., "Measurement of Blood Glucose", Ann. Clin. Biochem., 1985: 22: 327–342.

Japenburg, Rudolf, "Determination of Blood Glucose by Reflectance Spectroscopy, Reliability When Used in Clinical Routine", UPSALA Journal of Medical Sciences, vol. 91, iss. 2, 1986, pp. 173–174.

Zeller, H. et al., "Blood Glucose Measurement by Infrared Spectroscopy", International Journal of Artificial Organs, vol. 12, iss. 2, 1989, pp. 129–135.

FIG. 2
GLUCOSE

FIG. 3
PLASMA

GLUCOSE FLUORESCENCE MONITOR AND METHOD

BACKGROUND OF THE INVENTION

This invention relates generally to glucose monitors and, more particularly, to glucose monitors that determine the concentration of glucose in a sample by monitoring fluorescent light produced directly by glucose.

Glucose is a basic organic compound found in living organisms, food, and chemical products, and it is often advantageous to accurately determine the concentration of glucose in a sample. For example, a person having diabetes has lost the ability to produce insulin that regulates the sugar level in their blood. The affected persons must continually receive insulin injections and must regularly monitor the level of glucose in their blood to regulate the timing of the insulin injections. Glucose monitoring of the blood ordinarily requires that a small amount of blood be drawn from the body. Each time the skin of the body is penetrated to draw the blood, there is a risk of infection in addition to an associated buildup of scar tissue. In addition, considerable time is expended in drawing, processing and testing the blood.

Typical methods of determining the concentration of glucose in a sample, such as blood, fall into the categories of aromatic amine methods, enzymatic methods, oxidation methods, and most recently, infrared reflection and absorption spectroscopy. Infrared reflection and absorption spectroscopy in blood generally requires relatively complicated and expensive instrumentation and has limited resolution.

From the discussion above, it should be apparent that there is a need for a glucose monitor that is relatively noninvasive, that is simple and rapid to use, and that provides good resolution. The present invention fulfills these needs.

SUMMARY OF THE INVENTION

The present invention is embodied in a glucose monitor and related method that determines the concentration of glucose in a sample by monitoring fluorescent light produced directly by any glucose present in the sample. The glucose monitor illuminates the sample with excitation light that induces any glucose in the sample to fluoresce, with the fluorescent light being detected and processed to determine the concentration of glucose in the sample.

The glucose monitor includes a light source, a sensor, and a processor. The light source emits excitation light that is directed at the sample to induce any glucose in the sample to fluoresce. The excitation light causes the sample to produce return light, which includes fluorescent light produced by any glucose in the sample. The sensor monitors the return light and generates two signals representing the intensity of light within two spectral wavelength bands. The first signal is indicative of the intensity of return light having a wavelength within a first wavelength band. The second signal is indicative of the intensity of light within a second wavelength band. The processor processes the two electrical signals to determine the concentration of glucose in the sample.

In a more detailed feature of the invention, the light source emits narrowband light having a wavelength between about 250 nanometers and about 350 nanometers. A typical narrowband ultraviolet light source is an excimer laser having a wavelength of 308 nanometers.

The first wavelength band includes a characteristic spectral peak of glucose fluorescence. The peak has a wavelength that is about 30 to 50 nanometers longer than the wavelength of the excitation light. Using an excimer laser, the wavelength of the characteristic spectral peak of glucose fluorescence is between 335 to 355 nanometers. The second wavelength band is a reference band and is chosen from the range of about 380 to 420 nanometers.

The sensor monitors the return light from the sample. In another more detailed feature of the invention, the sensor has more than one detector that simultaneously monitors the return light within the first and second wavelength band. In a sensor having two detectors, one detector determines the intensity of light within the first wavelength band and the other detector determines the intensity of light within the second wavelength band. Each detector provides a signal indicative of the intensity of light within the corresponding wavelength band.

The processor determines the ratio of the light-intensities for the two wavelength bands from the signals. The concentration of glucose in the sample is determined from the ratio of light intensities.

The sample may consist of a variety of compositions and may be of solid or liquid form. In monitoring the glucose levels in a person's mouth, the sample is the oral cavity tissues such as the gums or the base of the tongue.

In another more detailed feature of the invention, the sensor includes a dichroic filter used to separate the excitation light from the return light, a stop having a slit, and a prism used to separate the turn light into its spectral wavelengths. The sensor may include a spectrograph having a detector array which is connected to an optical analyzer.

In another more detailed feature of the invention, a waveguide is used to guide the excitation light from the light source to the sample. The same waveguide or another waveguide is used to guide the return light from the sample to the sensor. If fiber-optic waveguides are used, they may be held together in a bundle for ease of use.

In another more detailed feature of the invention, the waveguides are housed in a probe. The probe may take many forms depending upon the application. The probe may be a catheter for monitoring the concentration of glucose in an extra-corporal blood flow. The probe may also be adapted to percutaneously monitor the concentration of glucose in a person's body through the skin such as in the oral cavity tissues of the mouth.

Other features and advantages of the present invention should become apparent from the following description of the preferred embodiment, taken in conjunction with the accompanying drawings, which illustrate, by way of example, the principles of the invention.

DESCRIPTION OF THE PREFERRED EMBODIMENTS

As shown in the exemplary drawings, the present invention is embodied in a glucose monitoring system 10 for determining the concentration of glucose in a sample 12 by monitoring the fluorescence of glucose directly, without the use of fluorescent dyes or the use of other indirect methods. Also, the glucose fluorescence monitoring system uses relatively inexpensive instrumentation and provides better resolution than prior optical spectroscopy methods. The glucose fluorescence monitoring system is relatively noninvasive, gives immediate results and is easily adapted to most laboratory and clinical units. The monitoring system does not require drawing blood from the body since it can monitor the glucose concentration percutaneously thus eliminating the related blood processing techniques such as centrifugation, storing and other time consuming testing.

Figure 1:
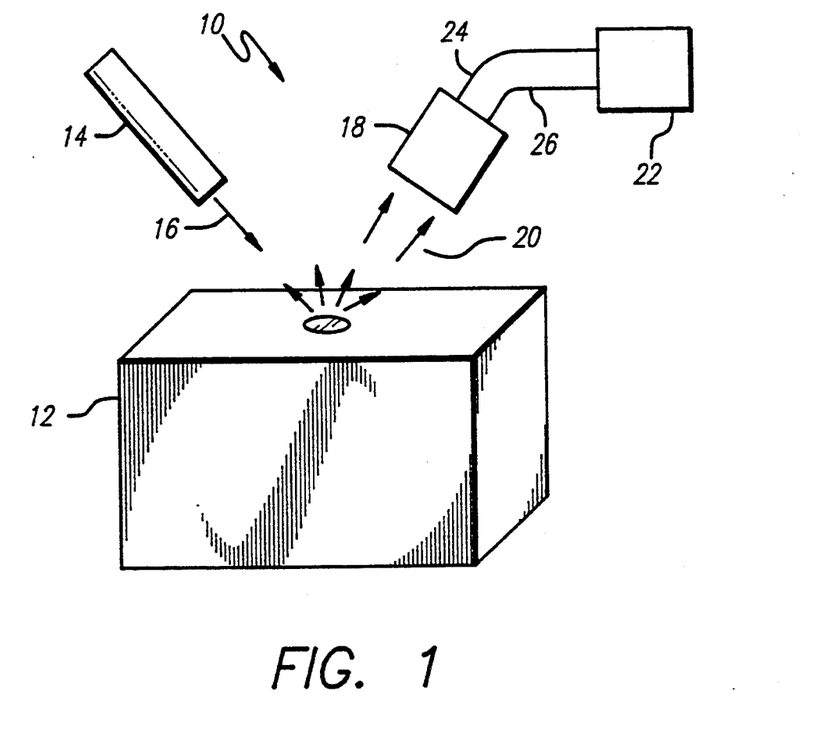
FIG. 1 is a block diagram of the glucose monitoring system embodying the invention.

In the glucose monitoring system 10 shown in FIG. 1, a light source 14 directs ultraviolet excitation light 16 at the sample 12, to induce any glucose within the sample to fluoresce. A sensor 18 monitors return light 20 from the sample, such return light including glucose fluorescence, and generates two electrical signals corresponding to the intensity of return light within two predetermined wavelength bands. The first electrical signal represents the intensity of return light within a wavelength band that includes a characteristic spectral peak of glucose fluorescence. The second electrical signal represents the intensity of return light within a reference wavelength band. The first and second electrical signals are communicated from the sensor to a processor 22 on lines 24 and 26, respectively. The processor then processes the two electrical signals to determine the concentration of glucose in the sample.

The light source 14 is also referred to as the excitation source. The excitation light 16 from the light source can have a wavelength from 250 nm to 350 nm. The excitation light can be produced from any type of narrow-band ultraviolet light source. In the preferred embodiment, the light source is an ultraviolet excimer laser having a wavelength of 308 nm and an energy density of 12 millijoules per square millimeter. Alternatively, a nitrogen laser, an optically-chopped helium-cadmium laser, a frequency-multiplied diode laser, or a solid-state laser can be used. The intensity or energy density of the excitation light should exceed one millijoule per square millimeter but should not exceed 15 millijoules per square millimeter. If the energy density is too high, ablation of the sample can occur, whereas if the energy density is too low, obtaining a sufficient electrical signal can be difficult.

The detectors in the sensor 18 can be as simple as individual light-sensitive diodes, with appropriate bandpass filters, or as complicated as an optical multichannel analyzer that analyzes a broad spectrum of the return light. Preferably, a simple CCD array is used to monitor a variety of wavelengths as desired with each individual cell monitoring a specific wavelength region.

In its simplest form, the processor 22 receives the electrical signals from the sensor 18 and almost instantaneously provides a ratio of the signals. The processor can further process the ratio to determine and indicate the presence, absence, or concentration of glucose in the sample 12.

Figure 2:
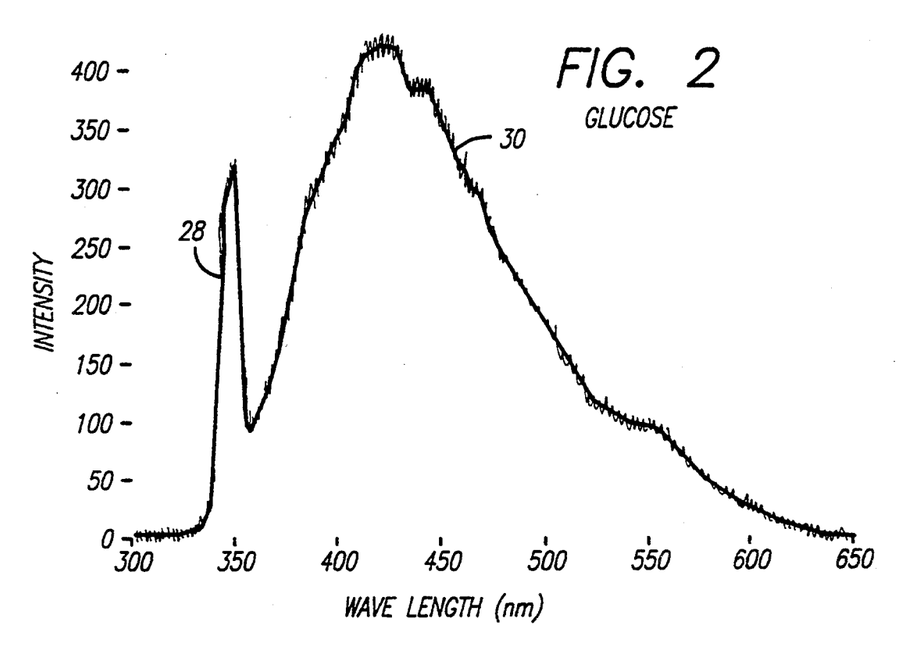
FIG. 2 is a graph of the intensity of glucose fluorescence versus wavelength when a glucose sample is illuminated with laser light having a wavelength of 308 nanometers.
Figure 3:
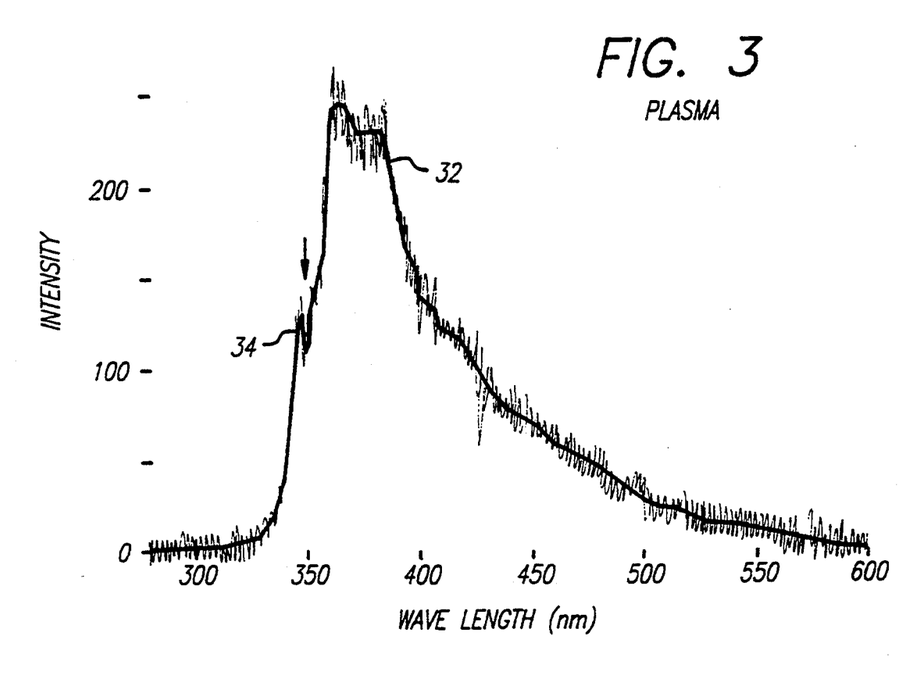
FIG. 3 is a graph of the intensity of plasma fluorescence versus wavelength when a human plasma sample is illuminated with laser light having a wavelength of 308 nanometers.
Figure 4:
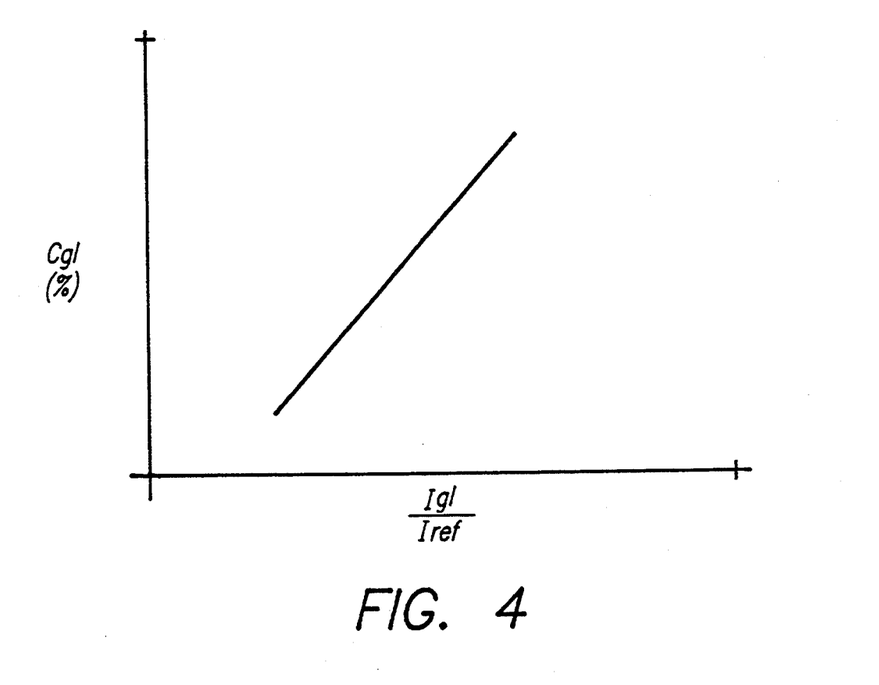
FIG. 4 is a graph of the concentration of glucose versus the ratio of the intensity of light in a wavelength band characteristic of glucose fluorescence to the intensity of light in a reference wavelength band.

The process of determining of the concentration of glucose in the sample is better understood with reference to FIGS. 2–4. The spectrum shown in FIG. 2 is the fluorescence spectrum of glucose after excitation with an ultraviolet excimer laser light having a wavelength of 308 nanometers. The spectrum is shown to have a double peak that is characteristic of all glucose solutions. One spectral peak corresponds to a broad fluorescence band 28 centered at approximately 440 nanometers, and the other spectral peak corresponds to a narrow fluorescence band 30 centered at approximately 345 nanometers. The wavelength of the peak of the narrow fluorescence band is approximately 30 to 50 nanometers longer than the wavelength of the excitation light. The narrow glucose fluorescence band is the characteristic wavelength band of glucose that is monitored to determine the concentration of glucose in the sample.

As shown in FIG. 3, the fluorescence spectrum of human plasma, when excited by ultraviolet excimer laser light having a wavelength of 308 nanometers, is distinct from the fluorescence spectrum of glucose. The fluorescence spectrum of human plasma has a broad fluorescence band 32 centered at approximately 380 nanometers and a narrow fluorescence band 34 centered at approximately 345 nanometers. The narrow fluorescence band 34 corresponds to the narrow fluorescence band 30 of glucose fluorescence and is indicated by a small peak having a wavelength that is approximately 30 nanometers shorter than the wavelength of the larger peak of the broad fluorescence band 32 of human plasma. The narrow fluorescence band 34 is the characteristic wavelength band of glucose fluorescence that is monitored to determine the concentration of glucose in the sample. The reference band is chosen from a wavelength band that is distinct from the narrow fluorescence band 34 of glucose fluorescence.

As disclosed in FIG. 4, the glucose concentration Cgl in the sample is determined from the ratio of measured light intensities within the desired wavelength bands (Igl/Iref). The first light intensity Igl represents the intensity of light measured within a first wavelength band corresponding to the characteristic wavelength band 34 of glucose fluorescence disclosed in FIG. 3. The second light intensity Iref represents intensity of light measured within a second wavelength band corresponding to the reference wavelength band. When using an excimer laser, the first wavelength band extends from about 335 nanometers to about 355 nanometers and the second wavelength band extends from about 380 nanometers to about 420 nanometers, or some portion thereof. The ratio Igl/Iref increases with increasing glucose concentration in the sample. The exact relationship between the glucose concentration and the intensity ratio is empirically derived.

Figure 5:
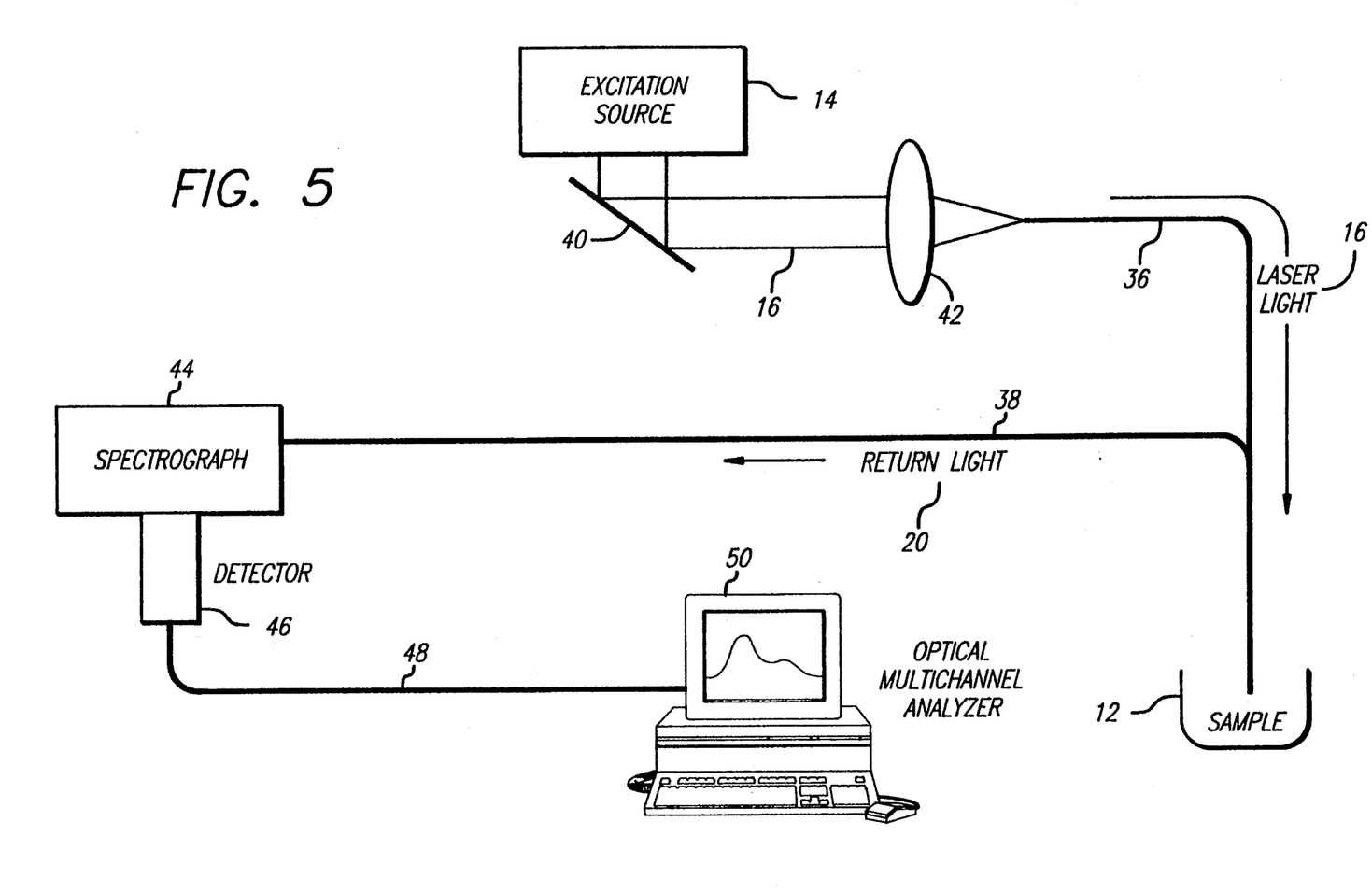
FIG. 5 is a block diagram of a first embodiment of a glucose monitoring system using fiber-optic waveguides.

FIG. 5 shows a first embodiment, in which the concentration of glucose in the sample 12 is determined by illuminating the sample and by capturing the resulting fluorescence spectrum using fiber-optic waveguides, 36 and 38. A first fiber-optic waveguide 36 guides the laser or excitation light 16 from the excitation source 14 to the sample. The excitation light is collimated when it is emitted from the excitation source and is directed toward the fiber using a mirror 40 that is highly reflective to ultraviolet light having a wavelength of 308 nanometers. The excitation light is focused into the first fiber-optic waveguide using a lens 42. The excitation light travels along the first fiber-optic waveguide to the sample.

The excitation light 16 causes the sample 12 to produce scattered return light 20 having a spectrum that depends upon the composition of the sample. The return light includes any reflected excitation light and the fluorescent light produced by the sample including fluorescent light produced by any glucose present in the sample. The return light is collected by a second fiber-optic waveguide 38 and is guided to and emitted unfocused towards the entrance of a spectrograph 44. At the entrance of the spectrograph is a long pass filter (not shown) having a cutoff wavelength of about 335 nanometers which excludes from the return light any reflected excitation light. Also at the entrance of the spectrograph is a slit having a width of 100 micrometers. The slit is followed by a diffraction grating having 150 grates per millimeter and a prism (not shown) that resolves the return light along an axis. A position along the axis corresponds to a wavelength of the return light.

Along the axis is positioned a detector 46, preferably a 1024-element charge-coupled device array. Each element of the detector array corresponds to a spectral wavelength of the return light. The detector array provides an analog signal 48 that is converted into a digital signal for determination of the concentration of glucose in the sample 12. The digital signal contains data representing the intensity of light received for each of the spectral wavelengths. The data may also be displayed on the screen of an optical-multichannel analyzer 50 or saved on a data disk. In the preferred embodiment, the detector is a 1024 element charge-coupled device array, part number EG&G 1422G.

The concentration of glucose in the sample 12 is calculated from the ratio of the light intensity collected in two spectral wavelength bands or regions. Using the data from the detector array, the intensity of light within the first wavelength band is compared with the intensity of light from the second wavelength band.

Figure 6:
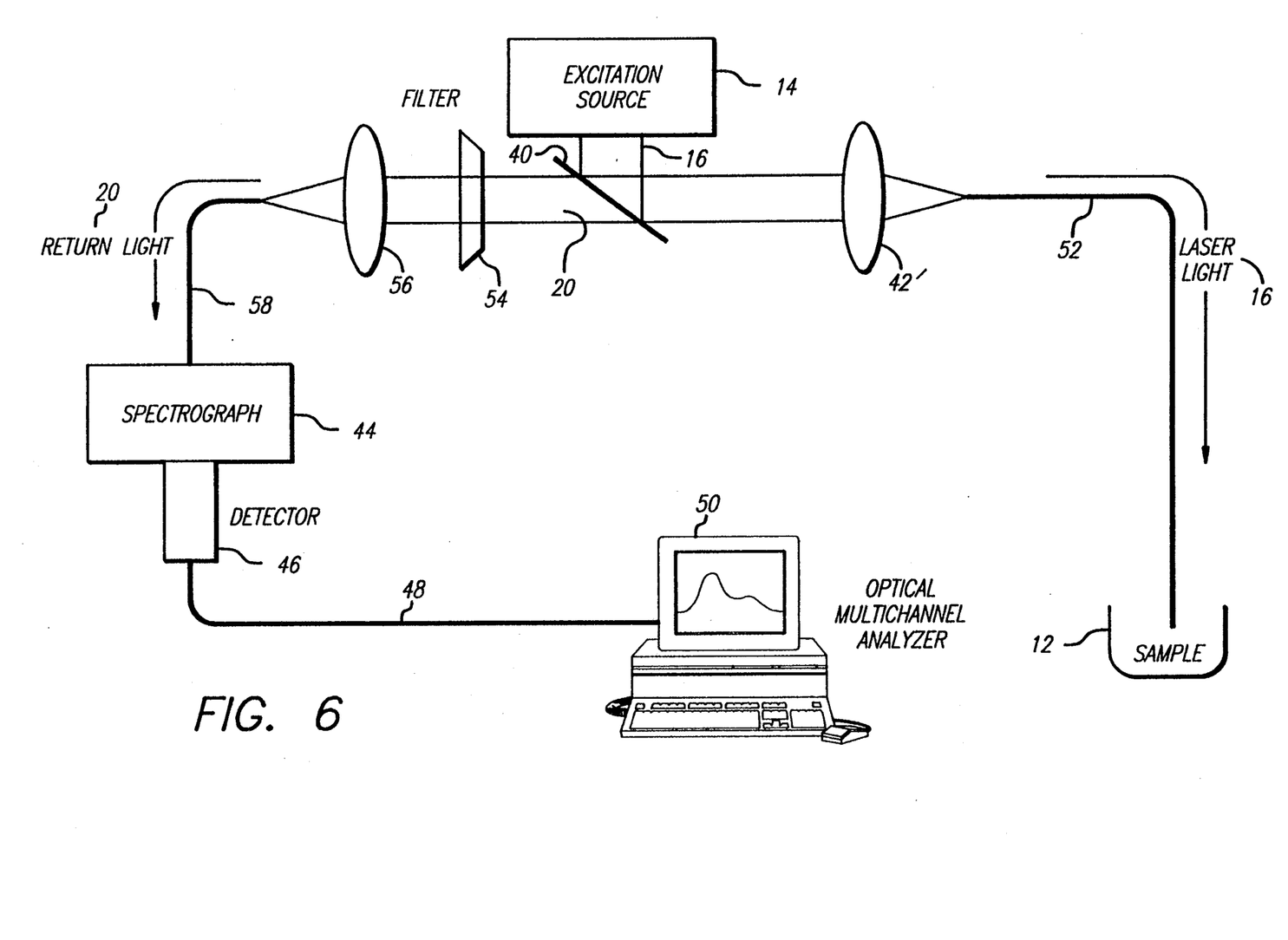
FIG. 6 is a block diagram of a second embodiment of a glucose monitoring system using a fiber-optic waveguide, which simultaneously carries excitation light to the sample and response light from the sample.

A related embodiment is shown in FIG. 6. This embodiment uses a single fiber-optic waveguide 52 to transmit the excitation light 16 to the sample 12 and to collect the return light 20 from the sample. A first lens 42' focuses the excitation light into the end of the fiber-optic waveguide 52 and also collimates the collected return light that is emitted from the fiber-optic waveguide. The collimated return light passes through the ultraviolet mirror 40 and through a long pass optical filter 54. The long pass optical filter has a cutoff wavelength of 335 nanometers to filter reflected excitation light from the return light. The fluorescent light is focused into another fiber-optic waveguide by a second lens 56. This second fiber-optic waveguide 58 transmits the return light to the entrance of a spectrograph. As discussed above, the spectrograph resolves the fluorescent light into its individual spectral components which are analyzed to determine the concentration of glucose in the sample.

Figure 7:
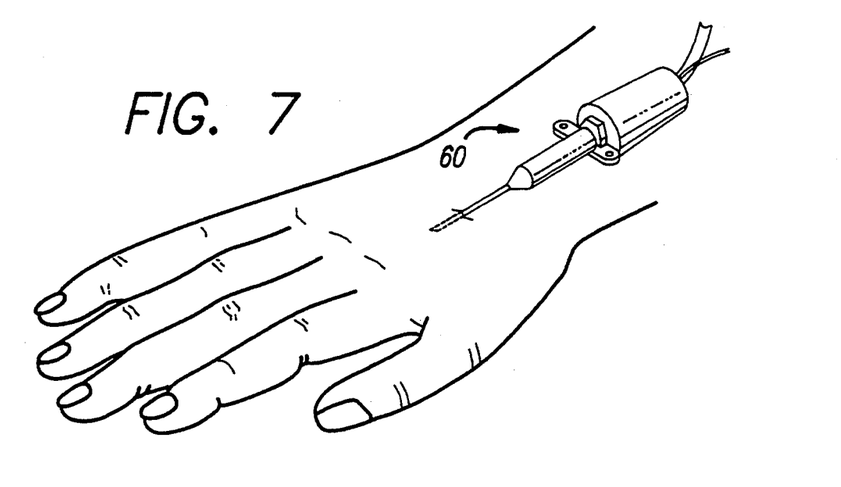
FIG. 7 illustrates a fiber-optic catheter for use in monitoring the concentration of glucose in a blood flow.

In yet another embodiment shown in FIG. 7, the waveguide is contained within a catheter 60. The catheter may contain one fused silica fiber or a bundle of many fibers. The catheter can be indwelling for use in an on-line monitoring system. It may also sense the glucose in an extra-corporeal blood flood, such as in a heart-lung machine or in a dialysis system.

Figure 8:
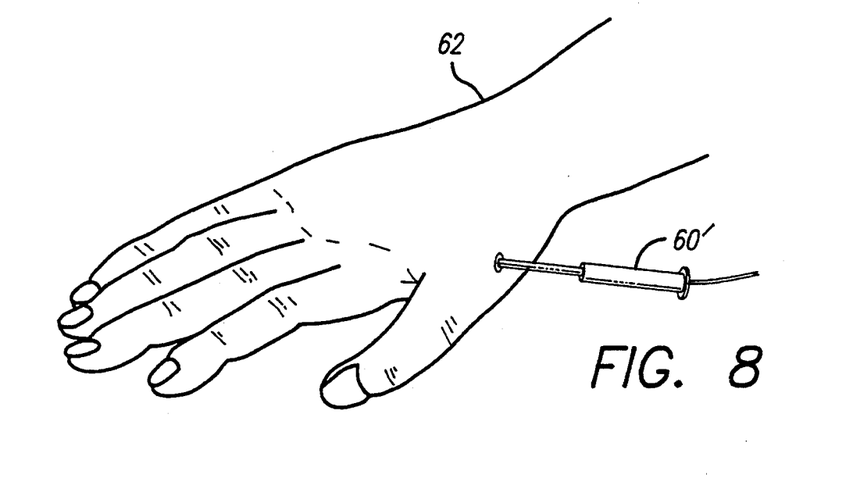
FIG. 8 illustrates a fiber-optic probe for use in monitoring the concentration of glucose in a person percutaneously.
Figure 9:
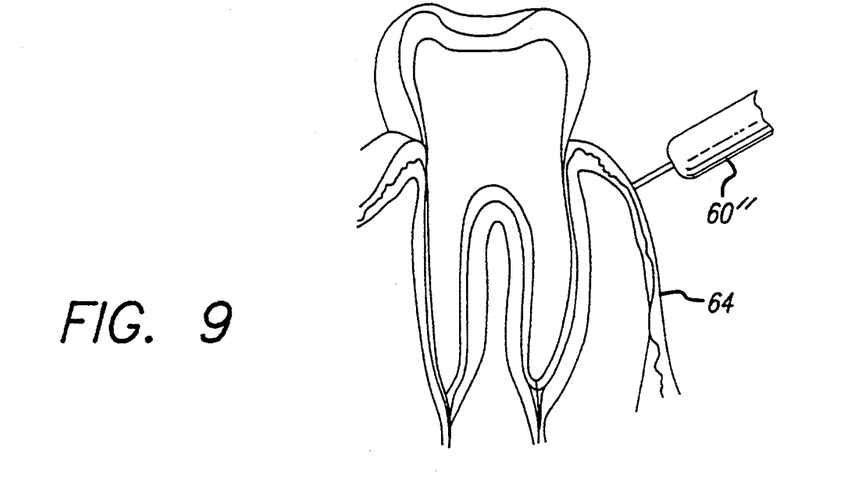
FIG. 9 illustrates a fiber-optic probe for use in monitoring the concentration of glucose percutaneously in the oral cavity tissues of a person's mouth such as the gums.

Alternative embodiments of the catheter 60 are shown in FIGS. 8 and 9. In FIG. 8, the catheter 60' is shown to monitor the glucose of a human body 62 percutaneously, or through the skin. In FIG. 9, the fiber-optic catheter 60" preferably is used to percutaneously monitor the glucose concentration in the oral cavity tissues of a person's mouth, such as the gums 64 or at the base of the tongue. Thus the glucose concentration in the human body can be monitored through this relatively noninvasive approach that uses ultraviolet fluorescence spectroscopy.

The glucose fluorescence monitoring system 10 functions with other bodily fluids as well as with solid organs. It is also applicable to a broad range of glucose sensing needs in food processes such as bread making, wine making and soft drink manufacturing. The glucose concentration within many translucent or transparent bodies can be monitored. Also, all kinds of biological and nonbiological fluids can be monitored including plasma, urine, soda, food products, wine, etc.

From the foregoing, it will be appreciated that the concentration of glucose in a human body can be monitored without requiring blood to be drawn from the body. The glucose monitor monitors the fluorescence of the glucose directly giving a direct determination of the glucose concentration. The fiber-optic waveguides simplify the delivery of the excitation light to the sample and the collection of the return light from the sample. The glucose monitor provides almost instantaneous monitoring of the glucose concentration.

Although the foregoing discloses preferred embodiments of the present invention, it is understood that those skilled in the art may make various changes to the preferred embodiments shown without departing from the scope of the invention. The invention is defined only by the following claims.

We claim:

1. Apparatus for determining the concentration of glucose in a sample, comprising:
   a light source that emits excitation light that is directed at a sample to produce return light from the sample, such return light including fluorescent light produced by any glucose present in the sample;
   a sensor that monitors the return light and generates a glucose fluorescence signal indicative of the intensity of return light within a wavelength band associated with the direct fluorescence of glucose and generates a reference signal indicative of the intensity of return light within a reference wavelength band; and a processor that processes the glucose fluorescence signal and the reference signal to determine the concentration of glucose in the sample.

2. Apparatus for determining the concentration of glucose in a sample, comprising:
   a light source that emits narrowband excitation light that is directed at a sample to produce return light from the sample, the excitation light having a wavelength between about 250 nanometers and about 350 nanometers;
   a sensor that monitors the return light and generates a first signal indicative of the intensity of return light within a first wavelength band, the first wavelength band being within a range that is about 30 to 50 nanometers longer than the wavelength of the excitation light, and wherein the sensor also generates a second signal indicative of the intensity of return light within a second wavelength band, the second wavelength band extending from about 380 nanometers to about 420 nanometers; and
   a processor that processes the first and second signals to determine the concentration of glucose in the sample.

3. Apparatus for determining the concentration of glucose in a sample as defined in claim 2, wherein:
   the wavelength of the excitation light is about 308 nanometers;
   the first wavelength band extends from about 335 nanometers to about 355 nanometers; and
   the second wavelength band extends from about 380 nanometers to about 420 nanometers.

4. Apparatus for determining the concentration of glucose in a sample as defined in claim 2, and further comprising one or more waveguides transmitting the excitation light from the light source to the sample and transmitting the return light from the sample to the sensor.

5. Apparatus for determining the concentration of glucose in a sample as defined in claim 4, wherein the one or more waveguides comprises:
   a first fiber-optic waveguide transmitting the excitation light from the light source to the sample; and
   a second fiber-optic waveguide transmitting the return light from the sample to the sensor.

6. Apparatus for determining the concentration of glucose in a sample as defined in claim 5, and further comprising a probe housing the one or more fiber-optic waveguides.

7. Apparatus for determining the concentration of glucose in a sample as defined in claim 6, wherein the probe is a catheter adapted to be placed in an extracorporeal blood flow.

8. Apparatus for determining the concentration of glucose in a sample as defined in claim 2, wherein the sensor includes:
   a first detector that detects the return light within the first wavelength band and generates the first signal; and
   a second detector that detects the return light within the second wavelength band and generates the second signal.

9. Apparatus for determining the concentration of glucose in a sample as defined in claim 2, wherein the sensor includes:
   a spectrograph having an array of detectors, the spectrograph resolving the return light such that each detector of the array detects a different spectral wavelength of the return light and generates a separate electrical signal representing the intensity of light in its wavelength; and
   an optical analyzer that analyzes the plurality of electrical signals from the spectrograph and generates the first and second signals.

10. Apparatus for determining the concentration of glucose in a sample as defined in claim 2, wherein the sensor comprises:
    a dichroic filter that rejects the return light having a wavelength equal to the wavelength of the excitation light and transmits the return light within the first and second wavelength bands;
    a stop having a slit aperture, wherein a portion of the return light that is transmitted through the dichroic filter passes through the slit;
    a prism that spreads the return light that passes through the slit such that the return light is spread along an axis by a distance proportional to the wavelength of the return light; and
    first and second electro-optical detectors that generates the first and second signals, respectively, the first electro-optical detector located along the axis at a distance corresponding to the first wavelength band and the second electro-optical detector located along the axis at a distance corresponding to the second wavelength band.

11. A method of determining the concentration of glucose in a sample, comprising:
    directing excitation light at a sample to cause the sample to produce return light, such return light including fluorescent light produced by any glucose present in the sample;
    monitoring the return light and generating first and second signals, the first signal indicative of the intensity of the return light within a first wavelength band and the second signal indicative of the intensity of return light within a second wavelength band; and
    processing the first and second signals to determine the concentration of glucose in the sample.

12. A method of determining the concentration of glucose in a sample, comprising:
    directing narrowband excitation light having a wavelength between about 250 nanometers and about 350 nanometers at a sample to cause the sample to produce return light, such return light including fluorescent light produced by any glucose present in the sample;
    monitoring the return light and generating first and second signals, the first signal indicative of the return light within a first wavelength band, the first wavelength band being within a range that is about 30 to 50 nanometers longer than the wavelength of the excitation light, and the second signal indicative of the intensity of return light within a second wavelength band; the second wavelength band extending from about 380 nanometers to about 420 nanometers; and
    processing the first and second signals to determine the concentration of glucose in the sample.

13. A method of determining the concentration of glucose in a sample as defined in claim 12, wherein:
    the wavelength of the excitation light used in the step of directing is about 308 nanometers;
    the first wavelength band used in the step of monitoring extends from about 335 nanometers to about 355 nanometers; and the second wavelength band used in the step of monitoring extends from about 380 nanometers to about 420 nanometers.

14. A method of determining the concentration of glucose in a sample as defined in claim 12, wherein the step of directing excitation light at a sample further comprises the step of guiding the excitation light to the sample.

15. A method of determining the concentration of glucose in a sample as defined in claim 12, wherein the step of monitoring the return light further comprises the step of guiding the return light from the sample.

16. A method for determining the concentration of glucose in a sample as defined in claim 12, wherein the step of monitoring the return light further comprises:
  detecting the return light within the first wavelength band to generate the first signal; and
  detecting the return light within the second wavelength band to generate the second signal.

17. A method of determining the concentration of glucose in a sample as defined in claim 16, wherein the step of monitoring the return light further comprises the step of resolving the return light into its different spectral wavelengths to detect the light within the respective first and second wavelength bands.

18. Apparatus for determining the concentration of glucose in the tissues of a person's mouth, comprising:
  a light source that emits excitation light;
  a first fiber-optic waveguide transmitting the excitation light from the light source to the tissues of a person's mouth to cause the tissues to produce return light, such return light including fluorescent light produced by any glucose present in the tissues;
  a sensor that monitors the return light;
  a second fiber-optic waveguide transmitting the return light from the tissues of the mouth to the sensor, wherein the sensor generates a glucose fluorescence signal indicative of the intensity of return light within a wavelength band associated with the direct fluorescence of glucose and generates a reference signal indicative of the intensity of return light within a reference wavelength band; and
  a probe housing the first and second fiber-optic waveguides, wherein the probe is adapted to enter the mouth; and
  a processor that processes the glucose fluorescence signal and the reference signal to determine the concentration of glucose in the tissues of a person's mouth.

19. A method of determining the concentration of glucose in a sample, comprising:
  directing excitation light at a sample to cause the sample to produce return light, such return light including fluorescent light produced by any glucose present in the sample;
  monitoring the return light and generating a glucose fluorescence signal and a reference signal, the glucose fluorescence signal indicative of the intensity of the return light within a wavelength band associated with the direct fluorescence of glucose and the reference signal indicative of the intensity of return light within a reference wavelength band; and
  processing the glucose fluorescence signal and the reference signal to determine the concentration of glucose in the sample.

* * * * *